(12) United States Patent  
Bergstedt et al.

(10) Patent No.: US 9,364,833 B2
(45) Date of Patent: Jun. 14, 2016

(54) MICRO-FLUIDIC MODULES ON A CHIP FOR DIAGNOSTIC APPLICATIONS

(71) Applicant: Lexmark International, Inc., Lexington, KY (US)

(72) Inventors: Steven W Bergstedt, Winchester, KY (US); Stephen J DeMoor, Georgetown, KY (US); Yimin Guan, Lexington, KY (US)

(73) Assignee: LEXMARK INTERNATIONAL, INC., Lexington, KY (US)

( * ) Notice: Subject to any disclaimer, the term of this patent is extended or adjusted under 35 U.S.C. 154(b) by 205 days.

(21) Appl. No.: 13/967,882

(22) Filed: Aug. 15, 2013

(65) Prior Publication Data

US 2014/0051159 A1 Feb. 20, 2014

Related U.S. Application Data

(60) Provisional application No. 61/684,599, filed on Aug. 17, 2012.

(51) Int. Cl.
*B01L 7/00* (2006.01)
*B01L 3/00* (2006.01)

(52) U.S. Cl.
CPC .............. *B01L 7/525* (2013.01); *B01L 3/50273* (2013.01); *B01L 2200/147* (2013.01); *B01L 2300/087* (2013.01); *B01L 2300/0816* (2013.01); *B01L 2300/0883* (2013.01); *B01L 2300/1827* (2013.01); *B01L 2300/1883* (2013.01); *B01L 2400/0442* (2013.01)

(58) Field of Classification Search
CPC ................... B01L 2200/147; B01L 2300/0816; B01L 2300/087; B01L 2300/0883; B01L 2300/1827; B01L 2300/1883; B01L 2400/0442; B01L 3/50273; B01L 7/525
See application file for complete search history.

(56) References Cited

U.S. PATENT DOCUMENTS

| 4,318,114 A | 3/1982 | Huliba |
| 6,283,718 B1 | 9/2001 | Prosperetti |
| 6,431,694 B1 | 8/2002 | Ross |

(Continued)

FOREIGN PATENT DOCUMENTS

WO    WO 2005094981 A1  *  10/2005

OTHER PUBLICATIONS

Jr-Hung Tsai; Liwei Lin, A Thermal-Bubble-Actuated Micronozzle-Diffuser Pump, Journal of Microelectromechanical Systems, Vo. 11, No. 6, Dec. 2002.

(Continued)

*Primary Examiner* — Nathan Bowers
*Assistant Examiner* — Lydia Edwards

(57) ABSTRACT

A chip having a substrate for amplifying genetic material includes a substrate heater having a plurality of substrate heating resistors. The heating resistors define a first temperature zone for maintaining a first temperature, a second temperature zone for maintaining a second temperature below the first temperature, and a third temperature zone for maintaining a third temperature between the first and second temperatures, on the substrate. A flow path formed on the substrate allows conveying of reactions to the first temperature zone, the third temperature zone, and the second temperature zone so as to undergo denaturing, annealing, and extension, respectively, according to a polymerase chain reaction process, for at least one cycle.

6 Claims, 10 Drawing Sheets

(56) References Cited

U.S. PATENT DOCUMENTS

| | | | |
|---|---|---|---|
| 6,655,924 B2 | 12/2003 | Ma | |
| 6,685,303 B1 | 2/2004 | Trauernicht | |
| 6,869,273 B2 | 3/2005 | Crivelli | |
| 7,374,274 B2 | 5/2008 | Cornell | |
| 2005/0009101 A1* | 1/2005 | Blackburn | 435/7.1 |
| 2009/0311713 A1* | 12/2009 | Pollack | B01L 3/502792 |
| | | | 435/287.2 |
| 2012/0007921 A1 | 1/2012 | Govyadinov | |

OTHER PUBLICATIONS

Jung-Yeul Jung; Ho-Young Kwak, Fabrication and Testing of Bubble Powered Micropumps using Embedded Microheater, Research Paper, Department of Mechanical Engineering, Chung-Ang University, Seoul, South Korea, Received Jun. 16, 2006, Accepted Aug. 1, 2006, Published online Sep. 16, 2006, Springer-Verlag.

D.J. Laser; J.G, Santiago, A review of Micropumps, Journal of Micromechanics and Microengineering, 14 (2004) p. R-35—R-64, Institute of Physics Publishing.

Jun el al., Microscale Pumping with Traversing Bubbles in Microchannels, Solid-State Sensor and Actuator Workshop, Hilton Head Island, SC, Jun. 3-6, 1996.

Chen, Zongyuan; Mauk, Michael G.; Wang, Jing; Abrams, William R.; Corstjens, Paul, L.A.M.;.Niedbala, R. Sam; Malamud, Daniel; Bau, Haim H., A Microfluidic System for Saliva-Based Detection on Infectious Diseases, Ann. N. Y. Acad. Sci 1098: 429-436 (2007) © 2007 New York Academy of Sciences doi: 10.1196/annals.1384.024.

Zhang, Chunsun; Xing, Da; Li, Yuyuan; Micropumps, microvalves and micromixers within PCR microfluidic chips: Advances and trends, Research review paper, pp. 483-514, MOE Key Laboratory of Laser Life Science & Institute of Laser Life Science, South China Normal University, No. 55, Zhongshan Avenue West, Tianhe District, Guangzhou 510631, PR China, Received Mar. 26, 2007; received in revised form May 6, 2007, accepted May 17, 2007, Available online May 23, 2007.

Zhang, Yonghao; Ozdemir, Pinar; Microfluidic DNA Amplification—a Review; Department of Mechanical Engineering, Univeristy of Strathclyde, Glasglow, G1 1XJ UK, pp. 1-26, Mar. 7, 2016.

STMicroelectronics—Microfluidics Division; Lab-on-Chip R&D; A highly integrated Lab on Chip device for rapid DNA testing in diagnostic applications; powerpoint slides, Mar. 7, 2016.

Mastrangelo, Carlos H.; Burns, Mark A.; Burke, David T.; Microfabricated Devices for Genetic Diagnostics; Proceedings of the IEEE, vol. 86, No. 8, Aug. 1998, pp. 1769-1787.

Roper, Michael G.; Legendre, Lindsay A.; Bienvenue, Joan M.; Ferrance, Jerome P.; Landers, James P.; Toward an Integrated Microdevice for DNA Extraction and PCR Amplification in the Submicroliter Regime for Forensic DNA Analysis; pp. 1-5, Mar. 7, 2016.

Joung, Seung-Ryong; Kim, Jaewan; Choi, Y.J.; Kim, Kang and Yong-Sang; ITO-coated glass/polydimethylsiloxane continuous-flow PCR chip; Proceedings of the 2nd IEEE International Conference on Nano/Micro Engineered and Molecular Systems; Jan. 16-19, 2007, Bangkok, Thailand, pp. 691-694.

Chen, Lin; Manz, Andreas; Day, Philip J.R.; Total nucleic acid analysis integrated on microfluidic devices; Critical Review, The Royal Society of Chemistry; Lab Chip, 2007, 7, pp. 1413-1423.

Erickson, David; Li, Dongqing; Integrated microfluidic devices; A review, Department of Mechanical and Industrial Engineering, University of Toronto, 5 King's College Road, Toronto, Ontario, Canada M5S 3G8; Received Aug. 6, 2003, accepted Sep. 3, 2003; pp. 11-26.

Day, Philip J.R.; Miniaturized PCR systems for cancer diagnosis; Biochemical Society Transactions (2009) vol. 37. part 2 pp. 424-426.

Foglieni, Barbara; Brisci, Angela; San Biagio, Floriana; Di Pietro, Patrizia; Petralia, Salvatore; Conoci, Sabrina; Ferrari, Maurizio; Cremonesi, Laura; Integrated PCR amplification and detection processes on a Lab-on-Chip platform: a new advanced solution of molecular diagnostics; Clin Chem Lab Med 2010; 48(3); pp. 329-336.

Yoon, Dae Sung; Lee, You-Seop; Lee, Youngsun; Cho, Hye Jung; Sung, Su Whan; Oh, Kwang W.; Cha, Junhoe; Lim, Geunbae; Precise temperature control and rapid thermal cycling in a micromachined DNA polymerase chain reaction chip; Institute of Physics Publishing, Journal of Micromechanics and Microengineering; Received Mar. 28, 2002, in final form Jul. 23, 2002, Published Oct. 3, 2002; pp. 813-823.

* cited by examiner

MICRO-FLUIDIC MODULES ON A CHIP FOR DIAGNOSTIC APPLICATIONS

FIELD OF THE INVENTION

The present invention relates to micro-fluid applications. More particularly, it relates to point-of-care and lab-on-a-chip devices having functional modules that enable diagnostic solutions.

BACKGROUND

Various diagnostic platforms utilize thermal cycling processes which involve heating of reagents at different temperatures to alter certain properties of the reagents. An example application is Polymerase Chain Reaction (PCR) which is a method used to amplify genetic material for detection and analysis. Analysis speed is especially important in diagnostic applications. For example, shorter analysis time would allow faster turnaround time in identifying infectious diseases, or enable the analysis to take place in the time it takes for a physician's appointment.

Thermal cycling methods generally fall under two categories: stationary and continuous flow. Stationary systems conduct thermal cycling by holding a fixed volume of sample fluid and/or reagents stationary in a chamber while varying the temperature of the chamber to alternately heat and cool the reagents. A disadvantage of this kind of thermal cycling is reduced amplification efficiency due to heating and cooling ramping rates associated with varying the chamber temperature during each cycle. Continuous flow systems, on the other hand, conduct thermal cycling by allowing fluid samples to flow through different temperature regions. In particular, each temperature region maintains a distinct temperature and reagents are allowed to pass through the temperature regions for a number of cycles by propelling them, using pumps, to flow through a long channel having sections formed on each temperature region. Delay in inter-temperature transition time can be reduced by controlling the flow rate of fluids within the channel. As a result, continuous flow systems can shorten analysis times compared to stationary thermal cycling.

A number of micro-fluidic approaches to diagnostic applications utilizing continuous flow thermal cycling have been developed for lab-on-a-chip and point-of-care devices. Micro-fluidic devices manipulate microscopic volumes of liquid inside micro-sized structures. As such, it can provide advantages over conventional and non-micro-fluidic based techniques such as smaller sample volumes, greater efficiency of chemical reagents, high speed analysis, high throughput, portability and low production costs per device allowing for disposability.

Micro-fluidic modules can be built by combining several components like channels, connectors, filters, mixers, heaters, sensors, micro-valves, micro-fluidic pumps, and etc. Among these components, it is well known to be difficult to attain micro-fluidic pumps which are ready to be assembled with micro-fluidic devices at low costs. For example, while a range of micro-fluidic devices have been miniaturized to the size of a postage stamp, these devices have often required large external pumping systems for fluid transport through channels. Unfortunately, the inclusion of these external pumps presents added complexity in coupling with fluidic channels, and also often increases the overall size of the micro-fluidic system.

Thus, there is a need for a micro-fluidic system which integrates together functional modules, such as pumps and micro-fluidic structures, to provide reliable and even smaller device footprint for point-of-care diagnostic and lab-on-a-chip applications. Additional benefits and alternatives are also sought when devising solutions.

SUMMARY

The above-mentioned and other problems become solved by forming pump modules and fluidic structures monolithically on a substrate to provide a micro-fluidic system on a chip. Example embodiments contemplate diagnostic solutions for polymerase chain reaction (PCR).

In a representative embodiment, a chip having a substrate for amplifying genetic material includes a substrate heater having a plurality of substrate heating resistors. The heating resistors define a first temperature zone for maintaining a first temperature, a second temperature zone for maintaining a second temperature below the first temperature, and a third temperature zone for maintaining a third temperature between the first and second temperatures, on the substrate. A flow path formed on the substrate allows conveying of reactions to the first temperature zone, the third temperature zone, and the second temperature zone so as to undergo denaturing, annealing, and extension, respectively, according to a PCR process, for at least one cycle.

In an example aspect, the flow path is formed by a flow feature layer disposed above the substrate heater. In another example aspect, one or more pumps are disposed along the flow path for compelling the reactions to move along the flow path.

These and other embodiments are set forth in the description below. Their advantages and features will become readily apparent to skilled artisans. The claims set forth particular limitations.

BRIEF DESCRIPTION OF THE DRAWINGS

The accompanying drawings incorporated in and forming a part of the specification, illustrate several aspects of the present invention, and together with the description serve to explain the principles of the invention. In the drawings.

DETAILED DESCRIPTION OF THE ILLUSTRATED EMBODIMENTS

In the following detailed description, reference is made to the accompanying drawings where like numerals represent like details. The embodiments are described in sufficient detail to enable those skilled in the art to practice the invention. It is to be understood that other embodiments may be utilized and that process, electrical, and mechanical changes, etc., may be made without departing from the scope of the invention. The following detailed description, therefore, is not to be taken in a limiting sense and the scope of the invention is defined only by the appended claims and their equivalents. In accordance with the features of the invention, a micro-fluidic system for thermal cycling integrates pump modules and fluidic structures on a single chip to enable diagnostic solutions. The modules are monolithically fabricated on a substrate using inkjet technology and heater chip fabrication techniques. In the following embodiments, representative diagnostic solutions contemplate a case study for polymerase chain reaction (PCR).

PCR is a process by which genetic material, such as DNA, is amplified exponentially for detection and analysis. PCR relies on cycling a mixture of ingredients including DNA sample, primers, and enzymes used for DNA synthesis, among others, through a series of repeated temperature changes, called cycles, to repeatedly heat and cool the mixture of ingredients. Typically, PCR has three thermal control steps/points for each cycle: denaturing, hybridization/annealing, and extension. During denaturing, a heating temperature above 90° C., such as from about 94° C. to about 98° C., breaks a double-stranded DNA molecule into two complementary single-stranded DNA molecules. In the annealing step, the single-stranded DNA molecules are cooled at a lower temperature from about 50° C. to about 65° C., such as about 60° C., to allow DNA synthesis whereby the single-stranded DNA molecules seek their complementary strands (designed primer) to create incomplete double-stranded DNA molecules. During the extension step, reactions are heated at a heating temperature above 65° C., such as from about 70° C. to about 75° C., so that the incomplete double-stranded DNA molecules are extended with the help of an enzyme called DNA polymerase. The cycle is then repeated a number of times to achieve a desired amount of amplification of the DNA material.

Figure 1:
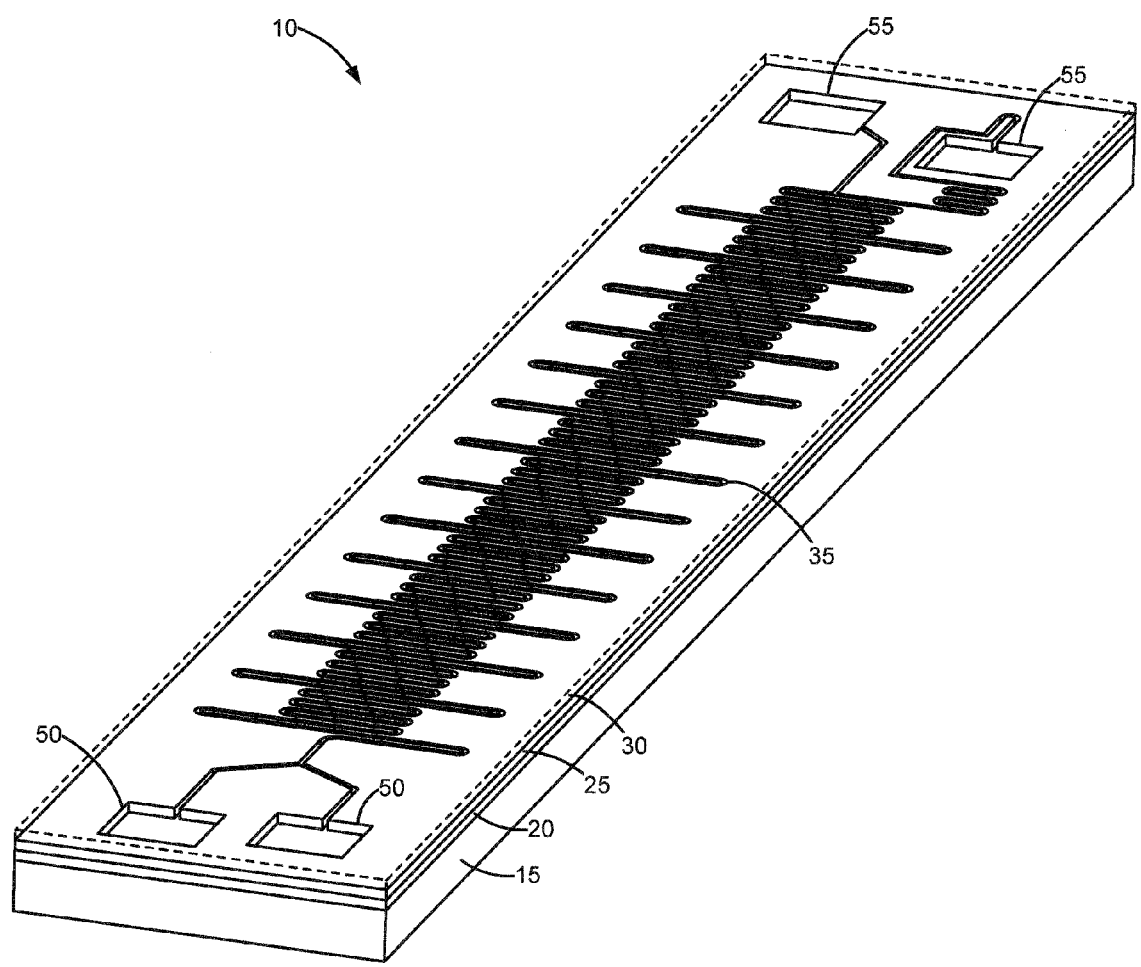
FIG. 1 is a perspective view of a micro-fluidic continuous flow PCR device, according to an example embodiment.
Figure 2:
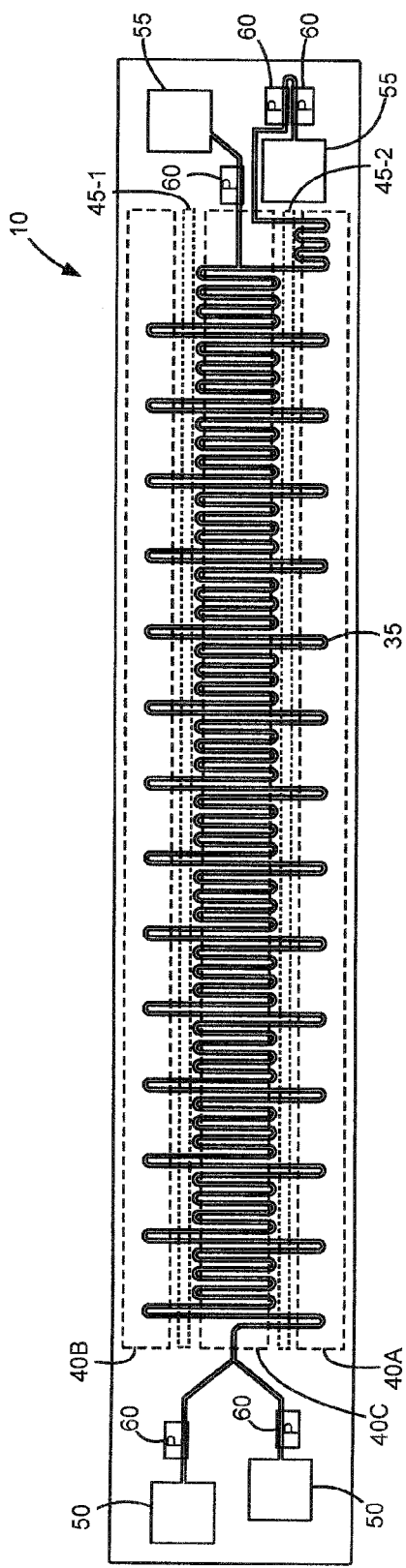
FIG. 2 is a top view of the PCR device in FIG. 1.

Referring now to FIGS. 1 and 2, there is illustrated an example embodiment of a micro-fluidic device and, more particularly, a continuous flow PCR (CF-PCR) device 10. CF-PCR device 10 includes a substrate 15, a heater layer 20, a flow feature layer 25 defining fluidic structures above the heater layer 20, and a cover layer 30 over the flow feature layer 25. The flow feature layer 25 defines walls and together with the cover layer 30 forms a channel 35 in which fluid flows. The channel 35 defines a serpentine channel having a plurality of cycles 35-1, 35-2, . . . , 35-n that extend along the length of CF-PCR device 10 through three distinct temperature regions 40A, 40B, and 40C, each region 40 for denaturation, annealing, and extension thermal control points of a PCR process, respectively. The temperature regions 40 are heated using heater elements formed and emplaced variously on heater layer 20 within each region 40, and are thermally isolated from each other by trenches 45 formed on the substrate 20 between each region 40, as will be explained in more detail below. Inlets 50 and outlets 55 formed at the ends of channel 35 serve to introduce and remove fluid from the channel 35. Any number of inlets and outlets can be formed.

Figure 3:
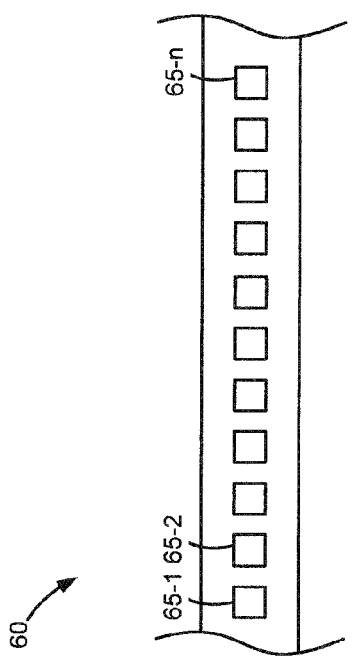
FIG. 3 is a schematic view of a micro-fluidic pump.

Pumps 60 are disposed along portions of channel 35 to propel fluid to flow the channel. In an example embodiment, each of pumps 60 includes a plurality of resistive heaters 65 (65-1, 65-2, . . . , 65-n) formed on heater layer 20 and along a corresponding channel portion, as shown in FIG. 3, to form a thermal bubble pump. In operation, by applying a voltage pulse to each of the heaters 65 of pumps 60, thermal bubbles are formed in a predetermined manner. For example, every heater 65 of pump 60 can form a bubble from the left to the right of the channel in sequence to push the liquid in the same direction. This cycle is then repeated to continue the pumping. Pumps of this type are the ones disclosed in more detail in U.S. patent application Ser. No. 13/556,495, filed Jul. 24, 2012, entitled "Micro-Fluidic Pump" and assigned to the assignee of the present invention. The disclosure of this patent is hereby incorporated herein by reference. As liquid is pumped through the channel 35, it repeatedly passes through the different temperature regions 40 for a number of cycles n to undergo thermal cycling. The residence time of a PCR reaction mixture within a temperature region 40 depends on the length of the channel within the region and the flow rate of the reaction within the channel 35. Accordingly, pumps 60 can be controlled to adjust the flow rate to achieve desired residence time.

Figure 4:
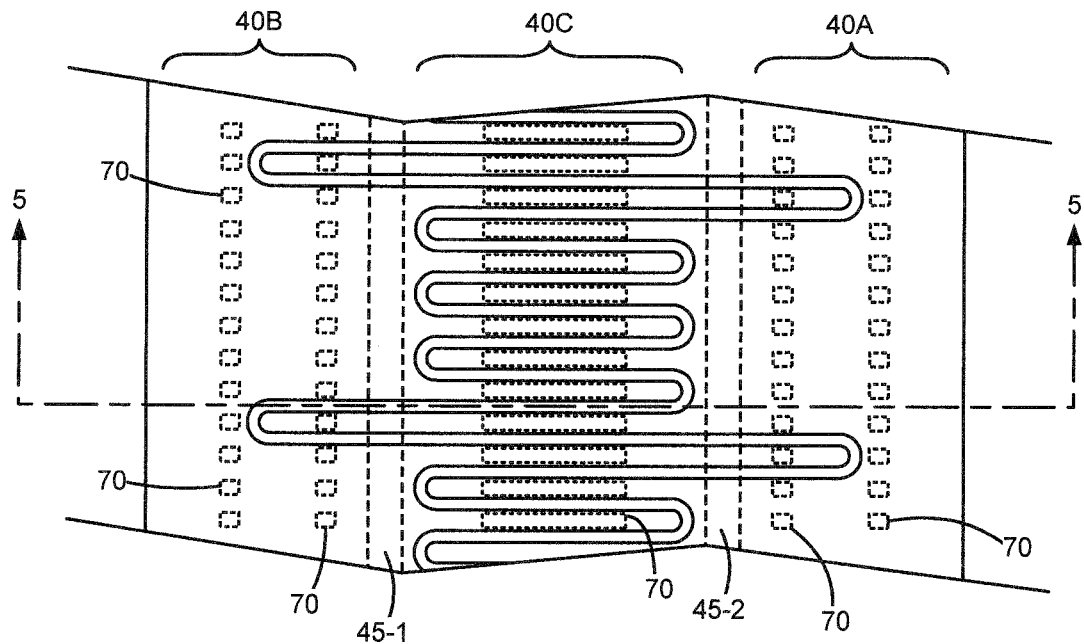
FIG. 4 illustrates a top view of a portion of the PCR device shown in FIG. 2.
Figure 5:
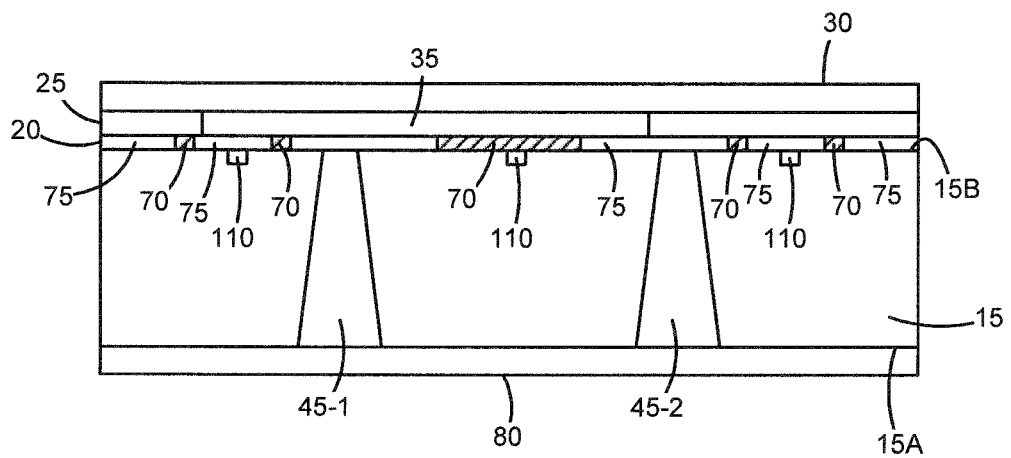
FIG. 5 shows a stack structure of the PCR device in FIG. 1 taken along line 5-5 of FIG. 4.

FIG. 4 illustrates a top view of a portion of CF-PCR device 10 with the cover layer 30 removed to show at least a cycle of the underlying channel 35, and FIG. 5 shows a stack structure of the CF-PCR device 10 taken along line 5-5 of FIG. 4. In FIG. 4, a plurality of heating elements 70 associated with each temperature region 40 are disposed at areas surrounding the channel 35, and trenches 45 are formed between temperature regions 40 for thermal isolation. By not disposing heating elements 70 along the channel 35, unequal heating of fluids within the channel can be avoided. Instead, fluids within each region 40 can be heated substantially equivalently or uniformly by allowing heat of the substrate to act on them, as will be explained in detail below. It will be appreciated that the depicted arrangement of heating elements 70 is only for purposes of illustration and thus should not be considered limiting, and that any number of heater elements and arrangement thereof on the substrate 15 can be used.

In FIG. 5, the stack shows heating elements 70 formed on the heater layer 20 above the substrate 15, a support material 75 surrounding the heating elements 70 to serve as underlying support for the channel 35, flow feature layer 25 formed above the heating elements 70 and support material 75, cover layer 30 formed above flow feature layer 25, trenches 45 etched from a backside 15A of the substrate 15 to a top surface 15B thereof, and a heat sink 80 beneath the substrate 15. (It should be noted that FIG. 5 is not an exact cross sectional view of FIG. 4. That is, cover layer 30 is present in FIG. 5 and the heating elements 70 are projected towards the cross sectional area such that they appear directly below the channel 35. Additionally, heat sink 80 which is not shown in FIG. 1 is shown in FIG. 5.)

The heating elements 70 are in thermal contact with the substrate 15 and the substrate 15 should be thermally conductive to dissipate heat from the heating elements 70. In operation, heat generated by the heater elements 70 travel through the substrate 15 and spreads out to each corresponding temperature region 40. Vertical heat flow from the substrate 15 dominates the temperature of the regions 40 and is used to heat fluids flowing through corresponding channels above the substrate 15. Trenches 45 serve to interrupt the travel of heat between temperature regions 40 to provide thermal stability. Additionally, heat sink 80 helps hold the lateral region to region heat flow to a minimum. In particular, with differing temperatures applied to each temperature region 40, a temperature gradient can be formed between adjacent temperature regions. Heat sink 80 collects heat residue between adjacent temperature regions 40 in order to substantially minimize the temperature gradient between regions.

Figure 6:
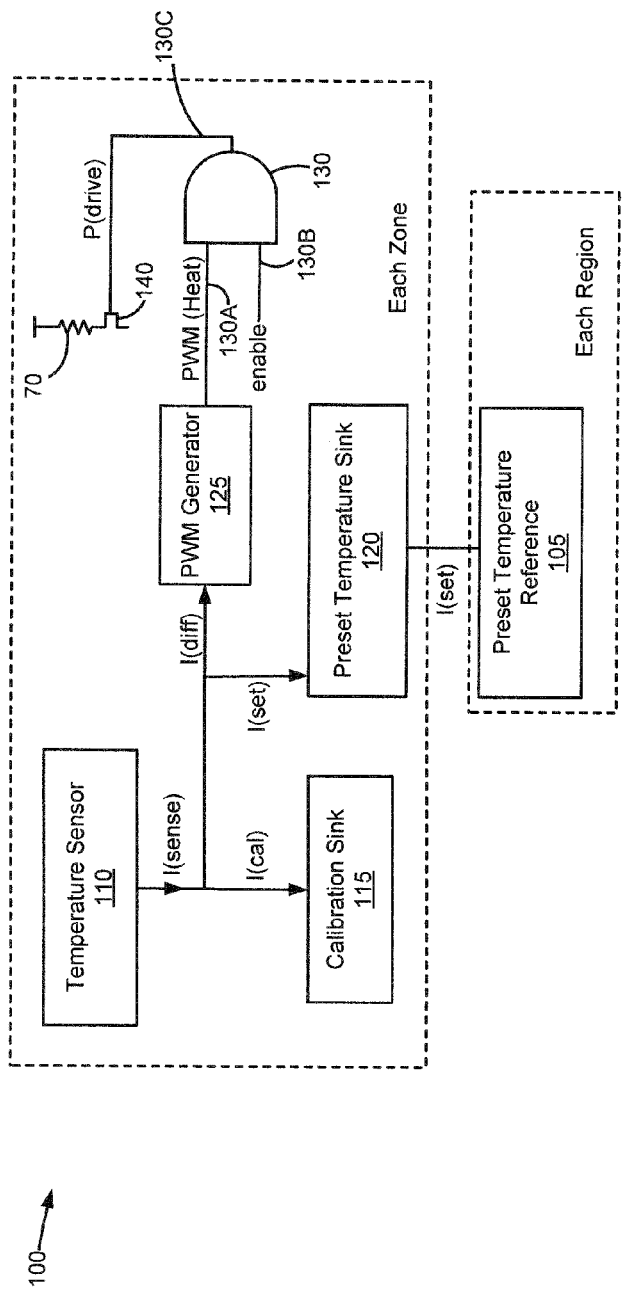
FIG. 6 is a schematic diagram of an on-chip thermal control system on the PCR device of FIG. 1, according to an example embodiment.

Referring now to FIG. 6, there is illustrated an on-chip thermal control system 100 that can be implemented integrally with CF-PCR device 10 and used to control each temperature region 40 to provide specific temperatures required for each thermal control point for PCR, in accordance with an example embodiment of the present invention. Generally, thermal control system 100 is used to sense the temperature of a temperature region 40 and limit temperature variations at desired levels. A number of the thermal control system 100 can be provided on CF-PCR device 10 to provide coverage for each of the temperature regions 40.

More particularly, for each temperature region 40, a thermal control system 100 includes a preset temperature reference source 105. Preset temperature reference source 105 can be an 8 bit digital to analog converter (DAC) connected to a serial peripheral interface, for example, that provides a desired temperature set point current input I(set) used to set the target temperature for a corresponding temperature region 40. Thermal control system 100 also includes at least one temperature sensor 110 that senses and provides actual substrate temperature readings in the form of a current input I(sense). Temperature sensor 110 can be an active circuit composed of CMOS transistors and substrate PNP which produces an output current proportional to absolute temperature sensed. In FIG. 5, temperature sensors 110 are shown as being formed on substrate 15 for each temperature region 40.

Figure 7:
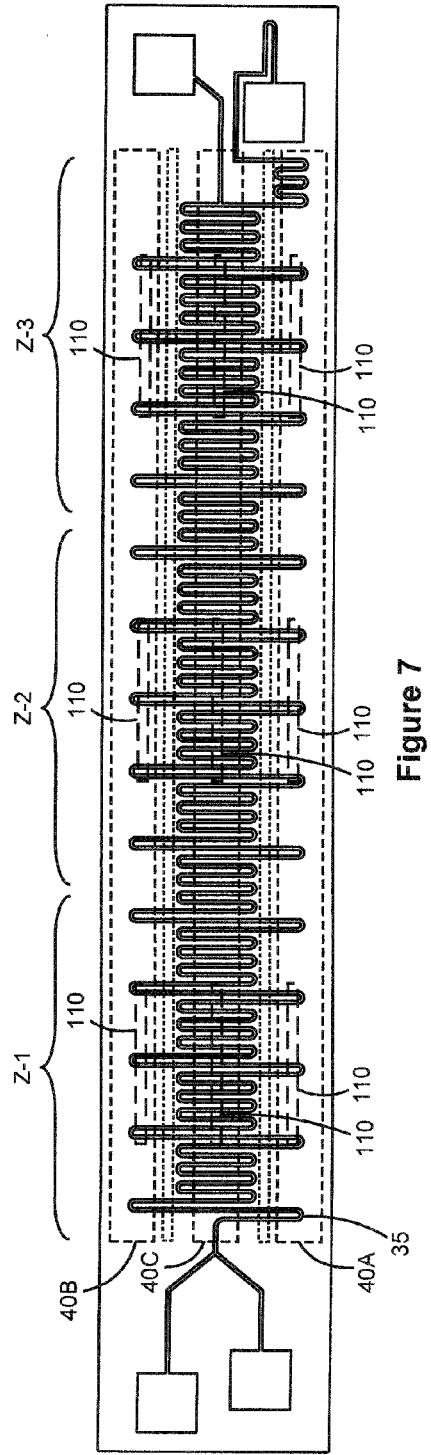
FIG. 7 is a top view of the PCR device in FIG. 1 showing temperature sensors disposed on different temperature regions and zones of the PCR device.

To provide more accurate temperature coverage of an entire length of a temperature region 40, each temperature region 40 may be divided into a plurality of zones with each zone having an associated temperature sensor. For example, as shown in FIG. 7, each temperature region 40 is divided into three zones Z-1, Z-2, Z-3 sensed by corresponding temperature sensors 110. Of course, each region can be divided into any number of zones. A calibration sink 115 may be provided to adjust for variations between zone temperature sensors 110 of each temperature region 40. In particular, calibration sink 115 may generate a calibration source current I(cal) from which each of the temperature sensors 110 of a region 40 may be calibrated. Accordingly, temperature sensors 110 associated with each temperature region 40 may read the same value for the same temperature after calibration.

Once the temperature sensors 110 are calibrated, the preset temperature reference current input I(set) is used to set the target temperature of each zone Z via a preset temperature sink 120. In particular, current input I(sense) from temperature sensor 110 and current input I(set) from preset temperature sink 120 combine to produce a current output I(diff) which is the difference between the current inputs. Essentially, current output I(diff) represents a difference between the target temperature and the temperature sensed by the temperature sensor 110. A pulse width modulation (PWM) generator 125 receives the current output I(diff) and outputs a pulse width modulated heat pulse PWM(heat) that is proportional to the current output I(diff). An AND gate 130 receives the heat pulse PWM(heat) at its input 130A. The other input 130B of AND gate 130 can be an enable signal for heating.

In an example embodiment, PWM generator 125 can be controlled to provide a set of quantized PWM signals during an initial thermal ramp up to a set point temperature. For example, PWM generator 125 could have a 5 phase quantized PWM signal having pulses with duty cycles of 100%, 75%, 50%, 25%, and 0%, during the initial ramp. The duty cycle is proportional to the current output I(diff) as discussed above. In this way, a smaller delay before reaching the set point temperature can be achieved.

Thermal control system 100 further includes a switch 140 connected to an output 130C of AND gate 130. The gates of switch 140 are driven by drive pulses P(drive) so that it periodically activates a connected heater element 70 to produce heat pulses that are delivered to the substrate 15. Heat then spreads throughout the substrate temperature region. Process then loops until the current I(sense) at each temperature sensor 110 is equal to the desired set current I(set) of the preset temperature sink 120 which corresponds to the required temperature for the temperature region 40. Accordingly, when the current input I(sense) from the temperature sensor 110 substantially equals the current I(set) from the preset temperature sink 120, the region is at its target temperature.

Figure 8:
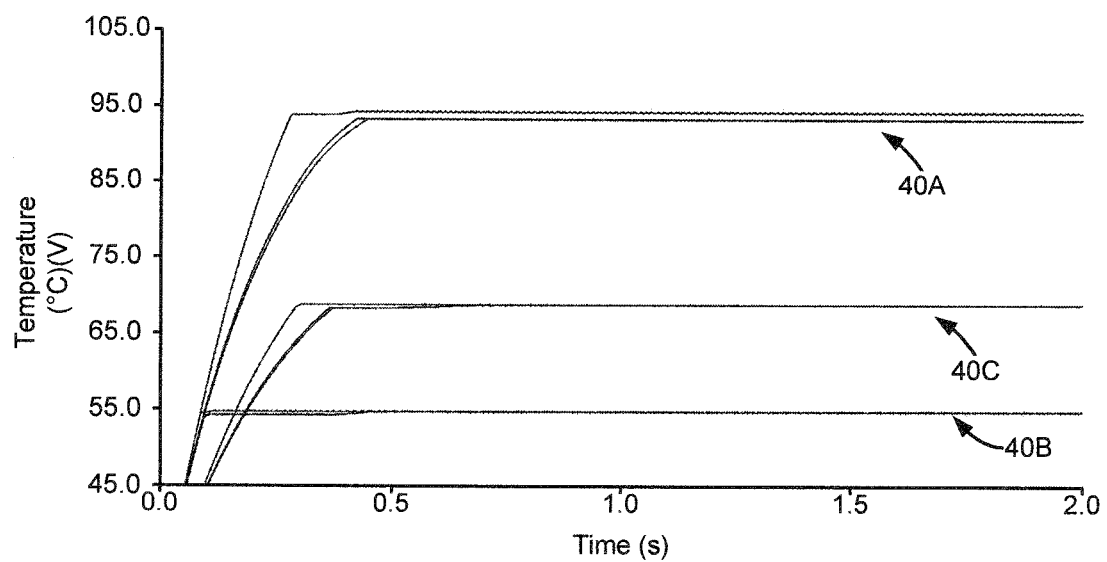
FIG. 8 is a simulation chart illustrating temperatures of each temperature region of the PCR device in FIG. 1, relative to time.

Thermal isolation structures, i.e., trenches 45, and heat sink 80 provide added stability in the thermal control. FIG. 8 shows a simulation chart illustrating temperatures of each of the regions 40 with respect to time. As shown, temperatures for each temperature region 40 are effectively maintained substantially linear after initial ramp. Additionally, temperature gradient along each temperature region 40 is kept minimal as indicated by the marginal deviation of thermal zone temperatures along each temperature region 40. Thus, the thermal control system 100 allows each temperature region 40 to be thermally stable within the range of its corresponding set point temperature.

CF-PCR device 10 is fabricated on substrate 15. The preferred substrate is silicon, which allows forming logic circuits together with the pumps and micro-fluidic structures. In addition, silicon provides high thermal conductivity to conduct heat from the heaters and heat fluids above it. The heating elements 70 associated with each region 40 and resistive heaters 65 associated with each pump 60 are formed by layers or films of semiconductor and other suitable materials formed or deposited, by using known micro-electronic fabrication techniques, on the substrate 15. For example, such heater elements 70 can be constructed in a similar fashion as the resistive heaters 65 as disclosed in U.S. Pat. No. 8,172,369, the contents of which are hereby incorporated by reference. Logic circuits to control heaters are formed on the substrate 15 by silicon processing. The heaters are then formed with the fluidic structures. A silicon dioxide is grown or deposited as the support material 75 on top of the substrate 15 (and alternatively over the heaters). A photoimageable polymer, for example, SU-8 (MicroChem, Newton, Mass.), is used to form the flow feature layer 25. For the cover layer 30, a photoimageable dry film, for example, VACREL™ (DuPont) is used and applied onto the flow feature by a lamination process. Inlet and outlet ports that align with inlets 50 and outlets 55 can be formed by either deep reactive ion etching (DRIE) or a photolithography process. By DRIE, an inlet port and an outlet port can be formed by etching holes through the substrate. In this case, liquid is fed into inlets 55 and the channel 35 from the backside of the substrate 15. An inlet port and an outlet port can be formed on the top side of the CF-PCR device 10 by patterning the flow feature 25 and cover layer 30. In addition, both DRIE and photolithography processes can be used to make an inlet port on the top side and outlet port on the backside of the CF-PCR device 10. A highly thermal conductive material, such as Al, aluminum alloys, Cu, diamond or composite materials like copper-tungsten, can be used for heat sink 80 beneath substrate 15.

Figure 9:
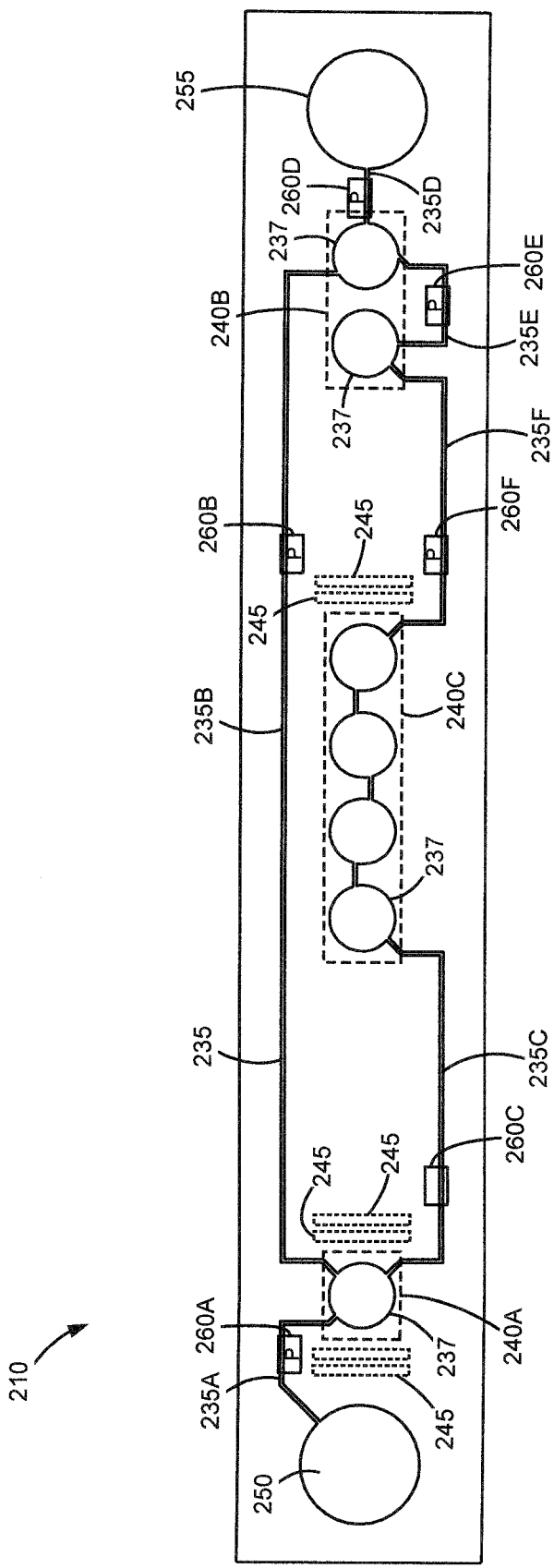
FIG. 9 is schematic view of a PCR device, according to another example embodiment.

Referring now to FIG. 9, another example embodiment of a micro-fluidic PCR device 210 is illustrated. Generally, PCR device 210 is fabricated using the same fabrication techniques as the CF-PCR device 10 discussed above, but with fluidic structures patterned to form a looped channel 235 containing a plurality of wells 237 formed on three thermal regions 240A, 240B, 240C, each region for denaturation, annealing, and extension thermal control points of a PCR process, respectively. Any number of wells for each region 240 can be utilized, depending on the design contemplated. The thermal regions 240 are heated using heater elements formed and emplaced variously within each region 240 and are thermally isolated from each other by trenches 245 formed between each thermal region 240. Inlet 250 and outlet 255 formed at the ends of looped channel 235 serve to introduce and remove fluid from the looped channel 35. A plurality of pumps 260 are disposed along portions of the fluidic structures of channel 235 to propel fluid.

In operation, fluids are propelled by pumps 260 through the looped channel 235 to pass through each of the thermal regions 240 to complete one thermal cycle. Depending on the required heating time, PCR reaction mixtures can be allowed to dwell within wells 237 of a thermal region 240 by deactivating pumps 260. Pumping can be continued to allow PCR reaction mixtures to repeatedly pass through the different thermal regions 240 for a required number of cycles depending on the amount of amplification desired. Pumps 260 can be controlled to pump fluids in a coordinated manner to properly direct fluid flow to desired fluid paths. For example, pumps 260A and 260B can be controlled to push fluids from left to right along channel portions 235A and 235B, respectively, while pump 260C is controlled to push fluids from right to left along a channel portion 235C to compel fluids within well 237 of thermal region 240A to flow towards channel portion 235B. Meanwhile, as pump 260B along channel portion 235B is controlled to push fluids from left to right, pumps 260D and 260E along channel portions 235D and 235E, respectively, can be controlled to push fluids from right to left to prevent fluids from flowing into outlet 255 and instead compel fluids within the wells 237 of thermal region 240B to flow towards channel portion 235F. To allow fluid flow into outlet 255, at least each of pumps 260B, 260D, and 260E can be controlled to push fluid from left to right to compel fluid within wells 237 of thermal region 240B to flow into outlet 255. As will be appreciated, other techniques for controlling the pumps to convey fluids within the channel can be implemented.

Figure 10:
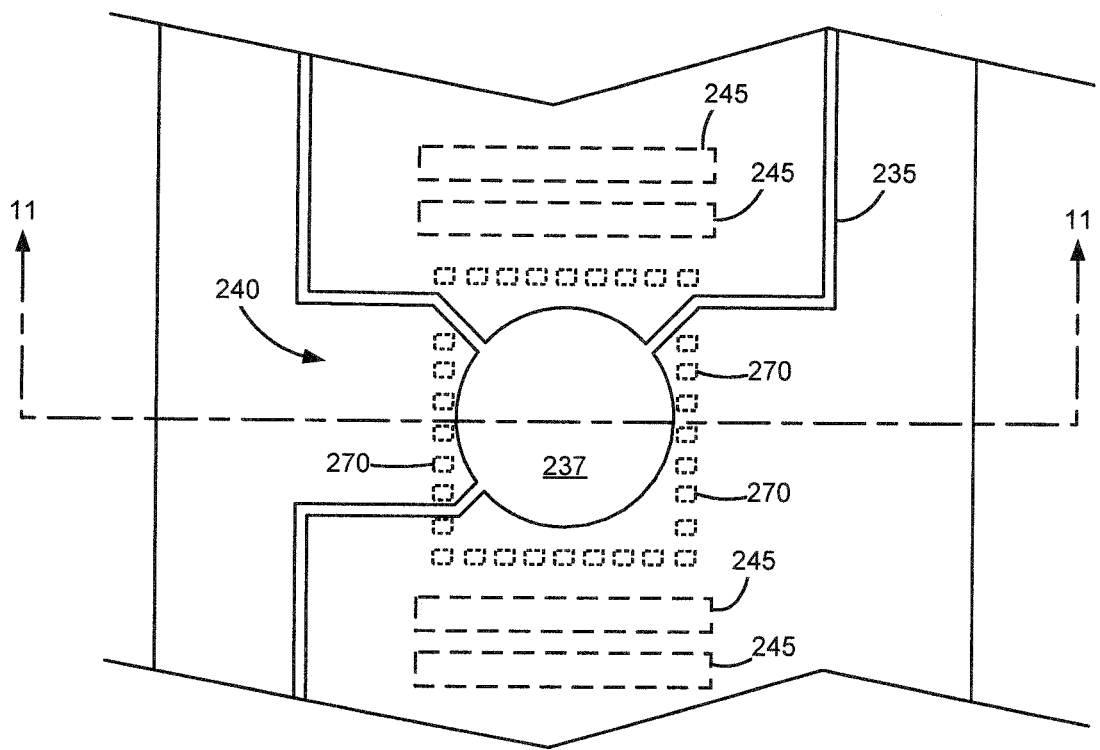
FIG. 10 illustrates a top view of a portion of the PCR device in FIG. 9.
Figure 11:
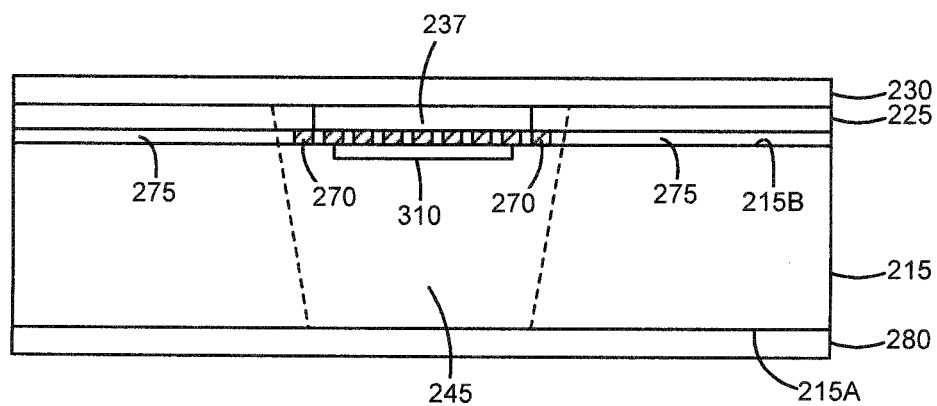
FIG. 11 shows a stack structure of the PCR device taken along line 11-11 of FIG. 10.

FIG. 10 illustrates a top view of a portion of PCR device 210 and FIG. 11 shows a stack structure of PCR device 210 taken along line 11-11 of FIG. 10. In FIG. 10, a plurality of heating elements 270 are disposed at areas surrounding the well 237 to define a thermal region 240. Different arrangements of heating elements can be utilized. Trenches 245 are also formed to thermally isolate the thermal regions 240. In FIG. 11, the stack shows heating elements 270 formed above and in thermal contact with a substrate 215, a support material 275 surrounding the heating elements 270 to serve as underlying support for the channels 235 and wells 237, a flow feature layer 225 formed above the heating elements 270 and support material 275 to provide upstanding walls for the channel, cover layer 230 formed above flow feature layer 225, trenches 245 etched from a backside 215A to a top surface 215B of the substrate 215 (and alternatively further through the support material 275 and the flow feature layer 225), and a heat sink 280 beneath the substrate 215. (It should be noted that FIG. 11 is not an exact cross sectional view of FIG. 10. That is, cover layer 230 above the flow feature layer 225 if illustrated in FIG. 10 would prevent the illustration of the underlying well 237. Hence, the cover layer 230 is not present in FIG. 10. In addition the heating elements 270 are projected towards the cross sectional area such that they appear directly below the well 237.) As previously mentioned, the heating elements 270, substrate 215, trenches 245, heat sink 280, and other similar components may be constructed in the same fashion and serve to provide the same functions as in the CF-PCR device 10 embodiment, the differences only being the pattern of the fluidic structures, location of the thermal regions and/or trenches, and specific pump functions.

Figure 12:
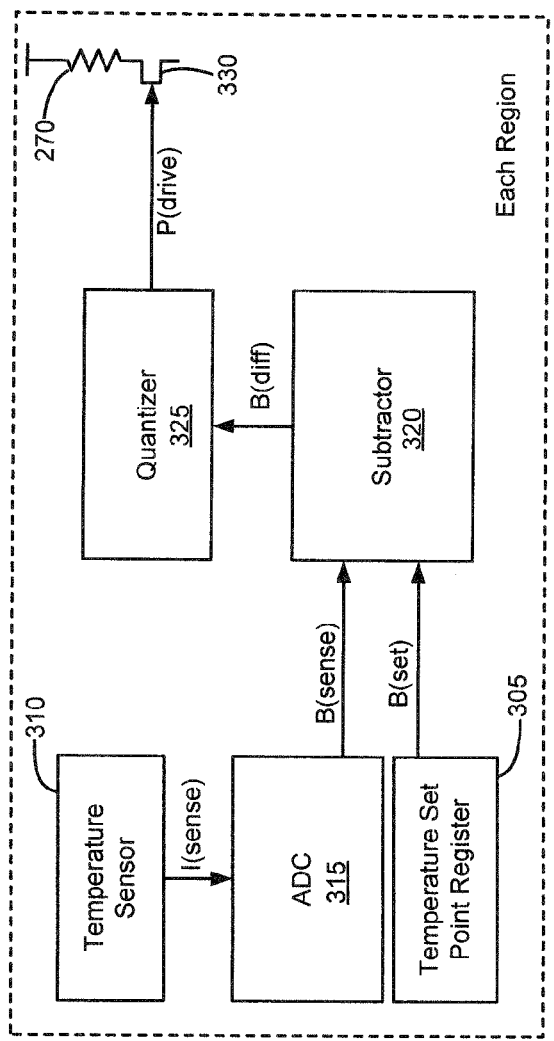
FIG. 12 is a schematic diagram of an on-chip thermal control system on the PCR device of FIG. 9, according to an example embodiment.

Referring now to FIG. 12, there is illustrated an on-chip thermal control system 300 that can be implemented integrally with PCR device 210 for each thermal region 240 to provide specific temperatures required for each thermal control point for PCR, in accordance with an example embodiment of the present invention. It should be noted, however, that the thermal control system 100 previously described can also be used for PCR device 210. Conversely, thermal control system 300 can also be used for CF-PCR device 10.

Figure 13:
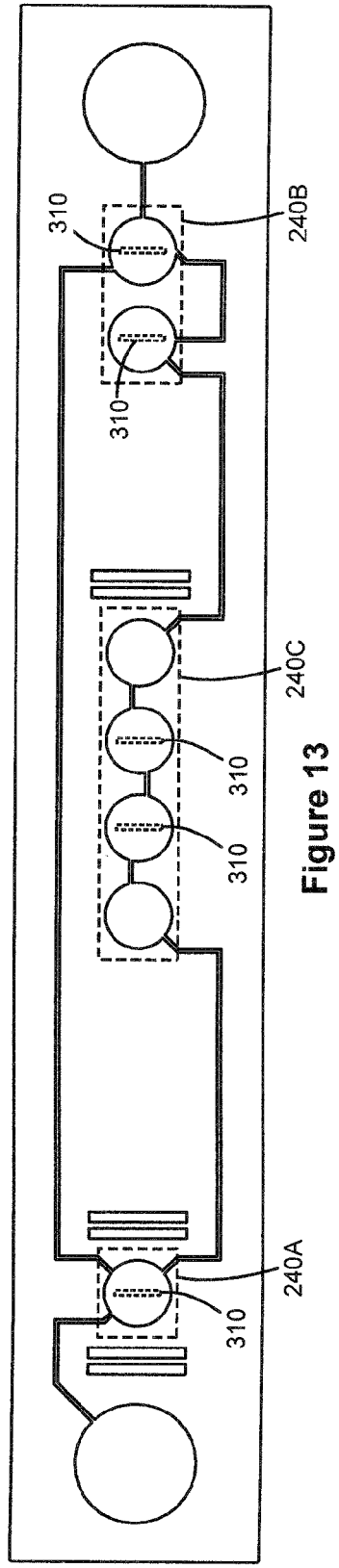
FIG. 13 is a top view of the PCR device in FIG. 9 showing temperature sensors disposed on different thermal regions.

Thermal control system 300 includes a temperature set point register 305 for holding a binary value B(set) corresponding to a target temperature. Thermal control system 305 also includes at least one temperature sensor 310 that senses and provides actual substrate temperature readings of a thermal region. Temperature sensor 310 can be an active circuit composed of CMOS transistors and substrate PNP which produces an output current I(sense) proportional to absolute temperature sensed. In FIG. 11, a temperature sensor 310 is shown as being formed on substrate 215. Any number of temperature sensors can be used for each thermal region to provide more accurate coverage. For example, as shown in FIG. 13, each of thermal regions 240B and 240C has two associated temperature sensors 310 defining thermal zones within each region.

Thermal control system 300 further includes an analog to digital converter (ADC) 315 that receives I(sense) from temperature sensor 310. ADC 315 can be an 8 bit ADC that samples and cycles through each thermal zone, sampling the output current I(sense) of temperature sensor 310 and converting it to an 8-bit binary value B(sense). A subtractor 320, which can be a 2's complement subtractor, receives as inputs the target temperature binary value B(set) from the temperature set point register 305 and the binary value B(sense) from ADC 315, and returns a value B(diff) that corresponds to the difference between the two inputs to a quantizer 325. Essentially, output B(diff) represents a difference between the target temperature and the temperature sensed by the temperature sensor 310. Quantizer 325 converts the difference output B(diff) of substractor 320 to a quantized PWM output P(drive) whose width is proportional to the difference output B(diff). The quantized PWM output P(drive) of quantizer 325 is then used to drive a switch 330 so that it periodically activates a connected heater element 270 to produce heat pulses that are delivered to the substrate 215. Heat spreads through the substrate thermal regions and the process loops until the binary value corresponding to the current I(sense) at temperature sensor 310 is equal to the binary value of the register 305 which corresponds to the target temperature for the thermal region. When B(sense) substantially equals B(set), the thermal region is at its target temperature.

Figure 14:
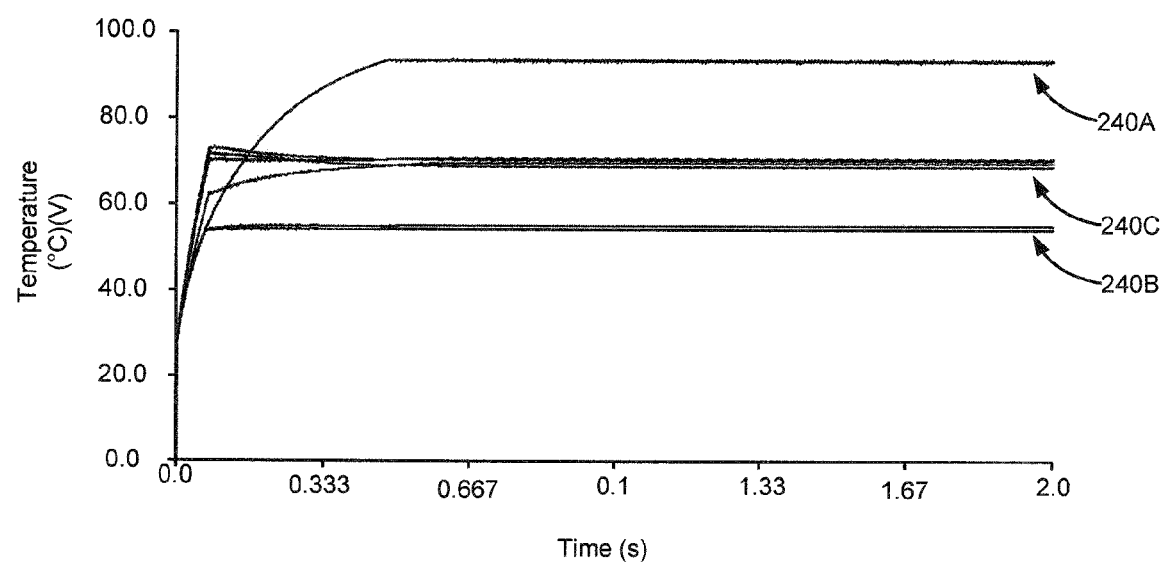
FIG. 14 is a simulation chart illustrating temperatures of each thermal region of the PCR device in FIG. 9, relative to time.

FIG. 14 shows a simulation chart illustrating temperatures of each of the thermal regions 240 with respect to time. As shown, temperatures for each thermal region 240 are effectively maintained substantially linear after initial ramp. Additionally, temperature gradient along each thermal region 240 is kept minimal as indicated by the marginal deviation of temperatures at arbitrary points selected in the top, bottom, and middle areas of a well for each thermal region 240.

Figure 15:
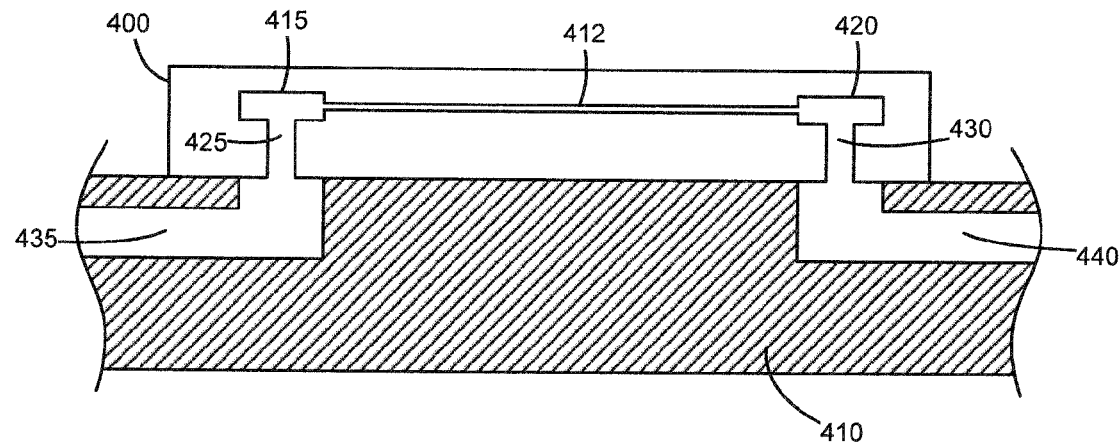
FIG. 15 is a diagram of a PCR device mounted as a lab-on-a-chip device, according to an example embodiment.

FIG. 15 shows an embodiment of a micro-fluidic PCR device 400, which can either be CF-PCR device 10 or PCR device 210, mounted on a lab-on-a-chip device 410. PCR device 400 has a channel 412, and inlet 415 and outlet 420 aligned with an inlet port 425 and an outlet port 430, respectively, formed through the substrate. Inlet port 425 and outlet port 430 are aligned and disposed on port holes 435 and 440, respectively, of the lab-on-a-chip device 410. A pressure sensitive adhesive or an epoxy adhesive can be used to bond the PCR device 400 on the chip 410.

Figure 16:
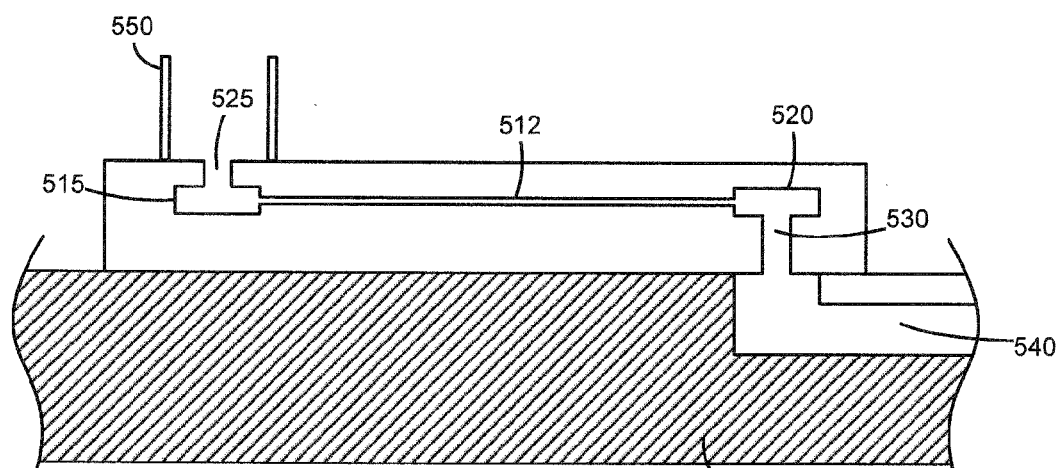
FIG. 16 is a diagram of a PCR device mounted as a lab-on-a-chip device, according to another example embodiment.

In another embodiment, a micro-fluidic PCR device 500 can have a top-side inlet 515 and bottom-side outlet 520, as shown in FIG. 16. The top-side inlet 515 aligns with an inlet port 525 formed by opening up the cover layer. On the other hand, DRIE of silicon can be used to form bottom-side outlet port 530 aligned with the outlet 520. PCR device 500 can be mounted on a lab-on-a-chip device 510. The outlet port 530 of PCR device 500 are aligned and disposed on a port hole 535 of the lab-on-a-chip 510. A liquid container 540 adjacent the inlet port 525 can be attached to introduce fluid into the inlet 515 and the channel 412.

Thus, micro-fluidic devices for point-of-care diagnostic and lab-on-a-chip applications are disclosed. The foregoing illustrates various aspects of the invention. It is not intended to be exhaustive. Rather, it is chosen to provide the best illustration of the principles of the invention and its practical application to enable one of ordinary skill in the art to utilize the invention, including its various modifications that naturally follow. All modifications and variations are contemplated within the scope of the invention as determined by the appended claims. Relatively apparent modifications include combining one or more features of various embodiments with features of other embodiments.

The invention claimed is:

1. A chip for amplifying genetic material, comprising:
a substrate having a top surface and a backside defining a thickness thereof;
at least two trenches through an entirety of the thickness of the substrate, each of the trenches being isolated from one another;
a substrate heater having a plurality of substrate heating resistors along a length of the substrate that define a first temperature zone for maintaining a first temperature, a second temperature zone for maintaining a second temperature below the first temperature, and a third temperature zone for maintaining a third temperature between the first and second temperatures, on the substrate, wherein one of the at least two trenches exists between the first and third temperature zones and the other of the at least two trenches exists between the second and third temperature zones thereby thermally isolating the substrate heating resistors in distinct temperature regions along the length of the substrate; and
a flow path formed on the substrate between a fluid inlet and outlet at ends of the length of the substrate for conveying reactions to the first temperature zone, the third temperature zone, and the second temperature zone to allow the reactions to undergo denaturing, annealing, and extension, respectively, according to a polymerase chain reaction process for at least one cycle, wherein the flow path extends in a flow feature layer on the substrate under a cover defining a serpentine channel having a plurality of cycles along an extent of the serpentine channel, wherein the cycles pass through each of the first, second and third temperature zones but wherein none of the substrate heating resistors are disposed in the cycles along the extent of the serpentine channel that passes above the at least two trenches.

2. The chip of claim 1, further comprising one or more pumps disposed along the flow path for compelling the reactions to move along the flow path.

3. The chip of claim 1, wherein the flow path is formed by a flow feature layer disposed above the substrate heater.

4. The chip of claim 1, wherein the first temperature is above 90° C.

5. The chip of claim 1, wherein the second temperature is between about 70° C. and about 75° C.

6. The chip of claim 1, wherein the third temperature is between about 50° C. and about 65° C.

* * * * *